United States Patent
Wilson et al.

[11] Patent Number: 5,876,201
[45] Date of Patent: Mar. 2, 1999

[54] DENTAL DEVICE AND METHODS

[76] Inventors: Audrey J. Wilson; Robert N. Wilson, both of 8971 S. Chestnut Hill La., Highlands Ranch, Colo. 80126

[21] Appl. No.: 919,979

[22] Filed: Aug. 28, 1997

[51] Int. Cl.[6] .................................................. A61C 17/02
[52] U.S. Cl. ............................................ 433/80; 433/140
[58] Field of Search .................................. 433/80, 82, 91, 433/93, 94, 95, 215, 229, 88, 140; 604/902, 275, 35, 36; 601/162, 166

[56] References Cited

U.S. PATENT DOCUMENTS

| | | | |
|---|---|---|---|
| 1,646,942 | 10/1927 | Tuorto | 433/88 |
| 3,086,524 | 4/1963 | Laws | 604/275 |
| 3,747,595 | 7/1973 | Grossan | 601/162 |
| 3,768,477 | 10/1973 | Anders et al. | 433/91 |
| 3,968,796 | 7/1976 | Baker . | |
| 4,975,054 | 12/1990 | Esrock | 433/80 |
| 4,984,984 | 1/1991 | Esrock | 433/88 |
| 5,197,875 | 3/1993 | Nerli | 433/80 |
| 5,242,300 | 9/1993 | Esrock | 433/80 |
| 5,306,146 | 4/1994 | Davis et al. | 433/80 |
| 5,342,195 | 8/1994 | Davis et al. | 433/80 |
| 5,376,003 | 12/1994 | Rizkalla | 433/116 |
| 5,542,845 | 8/1996 | Jenkins | 433/116 |

FOREIGN PATENT DOCUMENTS 3025023  1/1982  Germany ................................ 433/88

*Primary Examiner*—Cary E. O'Connor
*Attorney, Agent, or Firm*—Townsend and Townsend and Crew

[57] ABSTRACT

The invention provides exemplary devices and methods which are useful in treating an oral cavity. In one exemplary embodiment, a nozzle is provided which is adapted for attachment to a hand piece of a dental tool. The nozzle comprises an elongate body having a proximal end, a distal end, and at least one lumen extending between the proximal end and the distal end. The proximal end is adapted for attachment to the hand piece while the distal end is flared to facilitate manipulation of a body part.

16 Claims, 2 Drawing Sheets

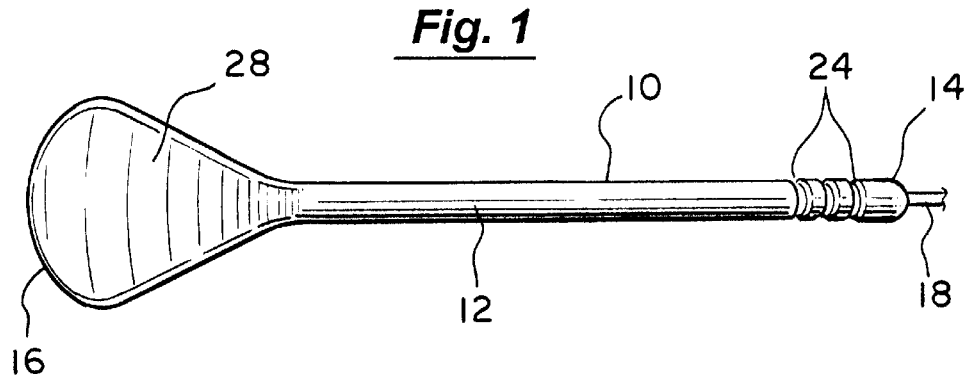
Fig. 1
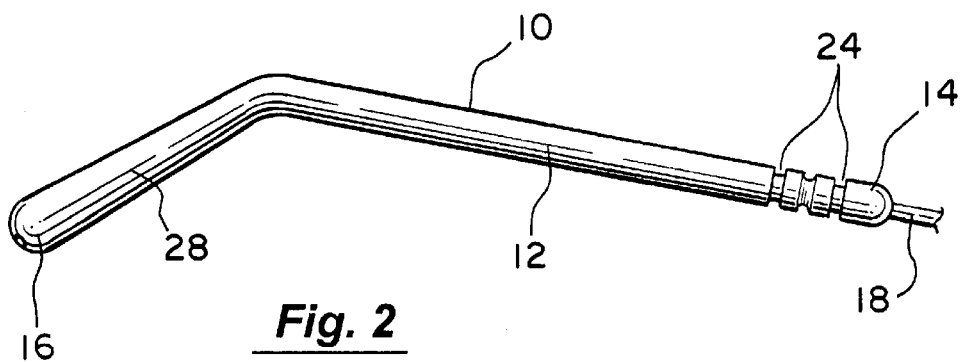
Fig. 2
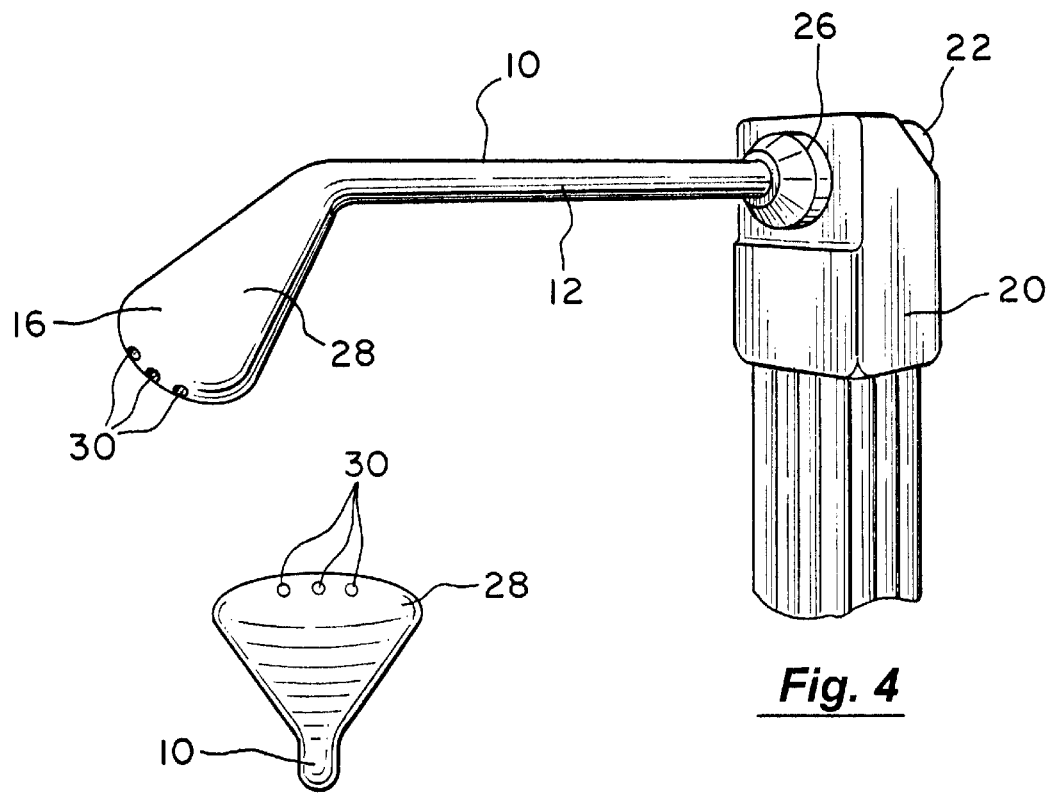
Fig. 3
Fig. 4

DENTAL DEVICE AND METHODS

BACKGROUND OF THE INVENTION

The invention relates generally to the field of dentistry, orthodontics and oral surgery, and more particularly to a dental tool. In a specific embodiment, the invention relates to a dental tool having a flared nozzle to facilitate retraction or manipulation of tissue during a dental procedure.

In many dental procedures, it is desirable to selectively supply air or water to a treatment area. A variety of dental tools have been developed to accomplish such a task. For example, a traditional dental tool is the air/water syringe which comprises a hand piece having a syringe tip which includes an air tube and a water tube which are joined together at the hand piece. Two operating buttons are provided on the hand piece to allow activation of the air or water. By depressing the air button, air flows out of the tip into the appropriate area of the patient's mouth to dry the treatment area. By depressing the water button, a flow of water is dispensed to clean away debris and congestion in the treatment area. When both buttons are simultaneously pressed, a spray of air and water is emitted to flush away debris which may then be vacuumed from the oral cavity. Such a dental tool is described in U.S. Pat. No. 3,874,083, the disclosure of which is herein incorporated by reference.

Various other dental tools have been proposed to provide various improvements to the traditional design. For example, U.S. Pat. Nos. 4,975,054; 4,984,984; and 5,242,300, the disclosures of which are herein incorporated by reference, describe nozzle assemblies which include separate air and water tubes to facilitate the delivery of two separate fluids to the oral cavity.

When performing a procedure within the oral cavity, it is often desirable to move the tongue, cheeks or lips in order to provide better access to the treatment area and direct the spray to a desired location within the oral cavity. The distal ends of existing air/water syringes are generally not well suited for such a task. For instance, when attempting to retract or manipulate the cheek, tongue or lips with the generally straight or somewhat pointed distal end of the nozzle, the tissue can easily become damaged or bruised. Use of a separate retraction instrument can also be undesirable as it requires the placement of an additional instrument into the oral cavity.

It would therefore be desirable to provide a dental tool having the ability to provide a supply of fluids, such as air or water, while also providing manipulation capabilities. Such a tool should be easy and convenient to use while also providing a relative degree of safety and comfort to the patient. In this way, the tissue in the oral cavity will generally be protected from bruises or other damage. It would further be desirable if such features could be accomplished by modifying existing dental air and water syringes in order to facilitate their introduction and acceptance into the dental market.

SUMMARY OF THE INVENTION

In one exemplary embodiment, the invention provides a nozzle which is adapted for attachment to a hand piece of a dental tool. The nozzle comprises an elongate body having a proximal end, a distal end and at least one lumen extending between the proximal end and the distal end. The proximal end is adapted for attachment to the hand piece, and the distal end is flared to facilitate manipulation of the tissue in and around the oral cavity. In this way, various fluids may be delivered to an oral cavity through the lumen while also providing manipulation and retraction capabilities using the flared distal end.

In one exemplary aspect, the lumen terminates in a plurality of orifices at the flared distal end. In this way, introduction of air or water into the oral cavity is facilitated. The flared distal end preferably has a major axis and a minor axis, with the major axis being longer than the minor axis. With such a configuration, the orifices are preferably distributed along the major axis. Such a configuration facilitates retraction of a body part, such as the cheek, tongue or lips, by engaging the body part with the flared distal end along the major axis and pulling on the nozzle. To further facilitate manipulation of the distal end, the elongate body may include a bend near the distal end.

In another aspect, the elongate body has a water lumen and an air lumen. Further, the distal end includes at least one orifice which is in communication with the air lumen, and at least one orifice which is in communication with the water lumen. In this way, the nozzle may include separate lumens for handling air and water distribution.

In another embodiment, the invention provides an exemplary dental tool which comprises a hand piece and a nozzle which is operably attached to the hand piece. The nozzle preferably comprises an elongate body having a proximal end, a distal end, and at least one lumen extending between the proximal end and the distal end. The proximal end is operably attached to the hand piece, and the distal end is flared to facilitate manipulation of a body part. The hand piece further includes at least one actuator to selectively control a supply of air and/or water through the lumen. In this way, the actuator may be actuated to allow air, water, or a combination of both to be supplied to an oral cavity. Further, the distal end may be employed to manipulate a body part in the oral cavity during procedures.

In one aspect, the lumen terminates in a plurality of orifices at the flared distal end. Preferably, the flared distal end has a major axis and a minor axis, with the major axis being longer than the minor axis. The orifices are preferably distributed along the major axis.

In an alternative aspect, the elongate body has a water lumen and an air lumen and orifices at the distal end to allow air, water, or a combination of both to be distributed into the oral cavity upon actuation of the actuator.

In still another embodiment, the invention provides an exemplary method for treating an oral cavity of a patient. According to the method, a nozzle of a dental tool is inserted into the oral cavity. The nozzle comprises an elongate body having a proximal end, a distal end, and at least one lumen extending between the proximal end and the distal end. Further, the distal end is flared. When within the oral cavity, tissue is engaged and manipulated with the flared distal end. Further, air, water or a combination of both is introduced into the oral cavity through the lumen. Hence, the method provides the ability to introduce air or water into the oral cavity to dry or clean away the desired area. Further, the distal end may be used to manipulate or retract tissue to gain access to a desired region, such as when vacuuming undesirable liquids from the oral cavity.

In one aspect of the method, the tissue comprises cheeks, lips or tongue of the patient. In another aspect, the lumen terminates in a plurality of orifices at the flared distal end to allow water or air to be selectively passed through the orifices.

In another aspect, the flared distal end has an elongate major axis which may be engaged with tissue to assist in retracting the tissue. Preferably, the orifices are distributed along the major axis. In still another aspect, the nozzle may be removed from the dental hand piece after use and then discarded or, if constructed of metal, sterilized for future use.

BRIEF DESCRIPTION OF THE DRAWINGS

FIG. 1 is a top view of an exemplary nozzle having a flared distal end according to the invention.

FIG. 2 is a side view of the nozzle of FIG. 1.

FIG. 3 is a front view of the nozzle of FIG. 1 showing the flared distal end.

FIG. 4 is a perspective view of an exemplary dental tool having the nozzle of FIG. 1 according to the invention.

DETAILED DESCRIPTION OF THE SPECIFIC EMBODIMENTS

Figure 5:
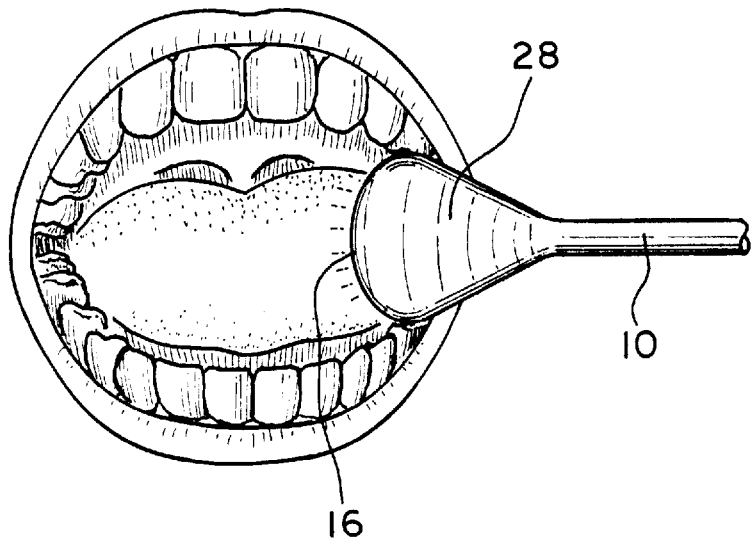
FIG. 5 illustrates an exemplary method for treating an oral cavity using the dental tool of FIG. 4.

The invention provides exemplary devices and methods for treating an oral cavity. In one exemplary embodiment, the invention provides a nozzle having a flared distal end. The nozzle includes at least one lumen to allow various liquids and/or air to be supplied to the oral cavity when the nozzle is attached to a conventional hand piece of an air/water syringe system used in many dental procedures. The flared distal end is preferably configured so that its geometry will facilitate retraction and/or manipulation of certain areas of the oral cavity during a dental procedure. In this way, the nozzle may be employed to both clean or dry a particular area and to retract or manipulate tissue in or around the oral cavity.

Referring now to FIGS. 1–3, an exemplary embodiment of nozzle 10 will be described. Nozzle 10 comprises an elongate body 12 having a proximal end 14 and a distal end 16. Extending between proximal end 14 and distal end 16 is a lumen (hidden from view). Proximal end 14 includes a tube 18 which is adapted to be inserted into a hand piece 20 (see FIG. 4) of a dental tool. Hand piece 20 is connected to a supply of fluids, typically to a supply of air and water. When tube 18 is inserted into hand piece 20, air, water, or both, may be delivered through the lumen upon operation of hand piece 20. In particular, hand piece 20 includes a pair of buttons 22 (one being hidden from view) which may be depressed to control the supply of air and/or water. When one of the buttons is depressed, air is introduced into tube 18 and through the lumen. When the other button is depressed, water will flow through tube 18. Finally, when both buttons are depressed, a mixture of air and water will be delivered through tube 18.

Proximal end 14 further includes various grooves 24 which cooperate with hand piece 20 and a securing nut 26 (see FIG. 4) to allow nozzle 10 to be removably attached to hand piece 20 as is known in the art. In this way, nozzle 10 may be used with commercially available hand pieces which are widely available. For example, such hand pieces may be purchased from a variety of commercial suppliers, including Brasseler U.S.A. Dental Rotary and Patterson Dental, both of Colorado.

Distal end 16 includes a flared portion 28, which includes a plurality of orifices. Orifices 30 are in communication with the lumen to allow air, water, or a spray of air and water to the exit nozzle 10 during operation of hand piece 20 as previously described. Flared portion 28 is shaped and sized so that it will be useful in manipulating and/or retracting various parts of the oral cavity during a procedure. For example, flared portion 28 may be used to retract and/or manipulate the lips, the tongue, the cheeks and the like. In this way, nozzle 10 is useful both as a cleaner (i.e., by spraying air and/or water through orifices 30) and as a retractor/manipulator. With such a configuration, a caregiver is able to provide two services to a patient with a single instrument. In this manner, use of separate retractor which may otherwise be painful to the patient and damaging to oral tissue, is eliminated.

Although a variety of shapes and orientations of distal end 16 may be provided in order to allow nozzle 10 to also function as a manipulator/retractor, flared portion 28 will preferably radially extend from body 12 by at least 10 mm, and more preferably in the range from about 15 mm to about 30 mm, and most preferably about 20 mm. A typical length for flared portion 28 will be in the range from about 25 mm to about 40 mm. Such a size is large enough to significantly prevent bruising and/or cutting of the oral cavity during a procedure. It is also small enough to allow distal portion 28 to be easily inserted into the oral cavity. Further, such a size allows for easy manipulation of nozzle 10 so that it may be used to clean various areas within the oral cavity during a procedure.

A variety of materials may be used to construct body 12. Exemplary materials for constructing body 12 include biocompatible plastics, metals, and the like. Preferably, flared portion 28 will be integrally formed with body 12.

Although shown with three orifices 30, it will be appreciated that various other numbers of orifices may be provided. Further, in some cases it may be desirable to provide multiple lumens extending through body 12. For example, if hand piece 20 were configured to provide air and water to separate lumens, body 12 could be modified to accommodate such a feature.

As best shown in FIGS. 2 and 4, flared portion 28 will preferably have cross-section having a major axis which is longer than a minor axis. Such a relatively flat configuration is particularly useful in grasping tissue within the oral cavity for manipulation and/or retraction. However, it will be appreciated that other related geometries may be provided for flared portion 28 in order to facilitate manipulation and/or retraction.

Referring now to FIG. 5, an exemplary method for using nozzle 10 will be described. Initially, nozzle 10 is attached to a hand piece of an air/water syringe as is known in the art. Nozzle 10 is then used in combination with other medical instruments used to treat oral cavities. For example, in the case of a simple cleaning, distal end 16 of the nozzle will be inserted into the oral cavity as shown. Air and/or water may then be introduced into the oral cavity through orifices 30 to dry or clean a particular area within the oral cavity. While cleaning the teeth, nozzle 10 may remain within the oral cavity and be employed to manipulate and/or retract the lips, tongue, cheek and the like, to gain access to the teeth or other areas in the oral cavity during the cleaning process. Periodically, air and/or water (or other similar liquids) may be introduced into the body cavity through orifices 30 as previously described.

Although described in the context of a cleaning procedure, it will be apparent that nozzle 10 may be useful in a wide variety of procedures within the oral cavity, including the treatment of cavities, root canals, oral surgery, orthodontic procedures, periodontal procedures, and other dental procedures.

In summary, nozzle 10 is advantageous in that a caregiver is able to retract and/or manipulate certain portions of the oral cavity with an air and water syringe without needing to introduce another retraction instrument into the oral cavity. Further, by providing the flared portion at the distal end of the nozzle, retraction and/or manipulation of tissue within the oral cavity may be accomplished without substantial bruising or cutting of the tissue.

The invention has now been described in detail for purposes of clarity of understanding. However, it will be appreciated that certain changes and modifications may be practiced within the scope of the appended claims.

What is claimed is:

1. A nozzle adapted for attachment to a hand piece of a dental tool, the nozzle comprising:

an elongate body having a proximal end, a distal end, and at least one lumen extending between the proximal end and the distal end, wherein the proximal end is adapted for attachment to the hand piece, wherein the distal end is flared to facilitate manipulation of a body part, wherein the flared distal end has a major axis and a minor axis, wherein the major axis is longer than the minor axis, wherein the minor axis has a length generally matching a cross sectional dimension of the body proximal of the flared distal end, wherein the lumen terminates in a plurality of orifices at the flared distal end, and wherein the orifices are distributed along the major axis.

2. A nozzle as in claim 1, wherein the elongate body includes a bend near the distal end.

3. A nozzle as in claim 1, wherein the elongate body has a water lumen and an air lumen, and wherein the flared distal end includes at least one orifice which is in communication with the air lumen, and at least one orifice which is in communication with the water lumen.

4. A dental tool, comprising:

a hand piece;

a nozzle comprising an elongate body having a proximal end, a distal end, and at least one lumen extending between the proximal end and the distal end, wherein the proximal end is operably attached to the handpiece, wherein the distal end is flared to facilitate manipulation of a body part, wherein the flared distal end has a major axis and a minor axis, wherein the major axis is longer than the minor axis, and wherein the minor axis has a length generally matching a cross sectional dimension of the body proximal of the flared distal end; and wherein the handpiece includes at least one actuator to selectively control a supply of air and a supply of water through the lumen.

5. A dental tool as in claim 4, wherein the lumen terminates in a plurality of orifices at the flared distal end.

6. A dental tool as in claim 5, wherein the orifices are distributed along the major axis.

7. A dental tool as in claim 4, wherein the elongate body includes a bend near the distal end.

8. A dental tool as in claim 4, wherein the elongate body has a water lumen and an air lumen, and wherein the flared distal end includes at least one orifice which is in communication with the air lumen, and at least one orifice which is in communication with the water lumen.

9. A method for treating an oral cavity of a patient, the method comprising:

inserting into the oral cavity a nozzle of a dental tool, the nozzle comprising an elongate body having a proximal end, a distal end, and at least one lumen extending between the proximal end and the distal end, and wherein the distal end is flared;

engaging and manipulating tissue in the vicinity of the oral cavity with the flared distal end; and introducing air or water to the oral cavity through the lumen.

10. A method as in claim 9, wherein the tissue comprises a cheek, a lip or a tongue.

11. A method as in claim 9, wherein the lumen terminates in a plurality of orifices at the flared distal end, and further comprising selectively passing water or air through the orifices.

12. A method as in claim 11, wherein the flared distal end has a major axis and a minor axis, wherein the major axis is longer than the minor axis, and further comprising retracting the tissue by engaging the flared distal end along the major axis with the tissue.

13. A method as in claim 12, wherein the orifices are distributed along the major axis.

14. A method as in claim 9, wherein the elongate body includes a bend near the distal end.

15. A method as in claim 9, further comprising removing the nozzle from the dental piece and discarding the nozzle after use.

16. A dental tool, comprising:

a hand piece;

a nozzle comprising an elongate body having a proximal end, a distal end, and at least one lumen extending between the proximal end and the distal end, wherein the proximal end is operably attached to the handpiece, and wherein the distal end is flared to facilitate manipulation of a body part;

wherein the handpiece includes at least one actuator to selectively control a supply of air and a supply of water through the lumen; and wherein the elongate body has a water lumen and an air lumen, and wherein the flared distal end includes at least one orifice which is in communication with the air lumen, and at least one orifice which is in communication with the water lumen.

* * * * *